United States Patent [19]
Crandell et al.

[11] Patent Number: 5,304,120
[45] Date of Patent: Apr. 19, 1994

[54] ELECTROPORATION METHOD AND APPARATUS FOR INSERTION OF DRUGS AND GENES INTO ENDOTHELIAL CELLS

[75] Inventors: Lois J. Crandell; Gunter A. Hofmann, both of San Diego, Calif.

[73] Assignee: BTX Inc., San Diego, Calif.

[21] Appl. No.: 907,322

[22] Filed: Jul. 1, 1992

[51] Int. Cl.$^5$ ............................................. A61M 31/00
[52] U.S. Cl. ..................................... 604/52; 604/21; 604/96; 604/102; 604/104; 606/41; 607/116
[58] Field of Search ................. 604/20, 21, 52, 96, 604/104, 113, 114; 606/32, 41, 42, 191, 198; 128/784, 783, 786; 607/115, 116, 122

[56] References Cited

U.S. PATENT DOCUMENTS

| | | | |
|---|---|---|---|
| 3,680,544 | 8/1972 | Shinnick et al. | 128/419 P X |
| 4,709,698 | 12/1987 | Johnston et al. | 604/114 X |
| 5,002,527 | 3/1991 | Reller et al. | 604/20 |
| 5,098,843 | 3/1992 | Calvin | 435/287 |
| 5,117,828 | 6/1992 | Metzger et al. | 128/642 |
| 5,137,817 | 8/1992 | Busta et al. | 435/173 |
| 5,154,165 | 10/1992 | Elliott et al. | 128/419 R |

FOREIGN PATENT DOCUMENTS

| | | | |
|---|---|---|---|
| 315982 | 5/1989 | European Pat. Off. | 604/96 |
| 1069826 | 1/1984 | U.S.S.R. | |
| 9116945 | 11/1991 | World Int. Prop. O. | 604/96 |
| 9207605 | 5/1992 | World Int. Prop. O. | |

Primary Examiner—C. Fred Rosenbaum
Assistant Examiner—Corrine Maglione
Attorney, Agent, or Firm—Baker, Maxham, Jester & Meador

[57] ABSTRACT

A catheter device is inserted into a selected blood vessel of a patient and advanced to a preselected location within the blood vessel where the endothelial cells on the inner wall of the vessel are to be treated. Once in place, the catheter device is expanded so that a plurality of axially extending, circumferentially spaced electrodes carried thereby are in contact with the inner wall of the blood vessel. A fluid medium is then infused into the blood vessel adjacent the electrodes via a conventional pump. A power pack connected to the electrodes is energized to apply a predetermined electric signal to the electrodes. This subjects the endothelial cells to electric fields of predetermined amplitude and duration in order to make the walls of the endothelial cells transiently permeable to permit therapeutic genes or drugs carried by the fluid medium to enter the endothelial cells without killing them.

18 Claims, 2 Drawing Sheets

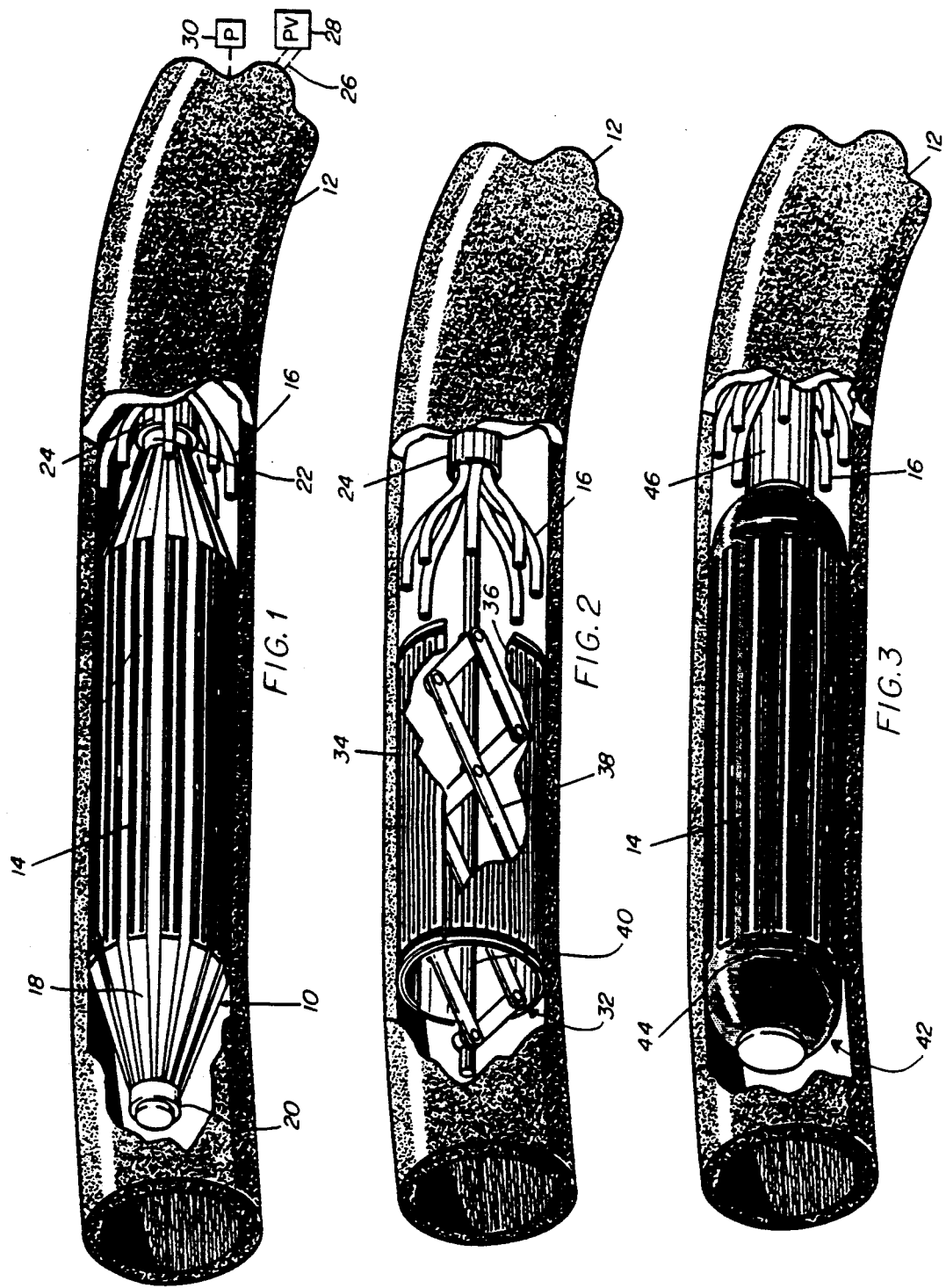

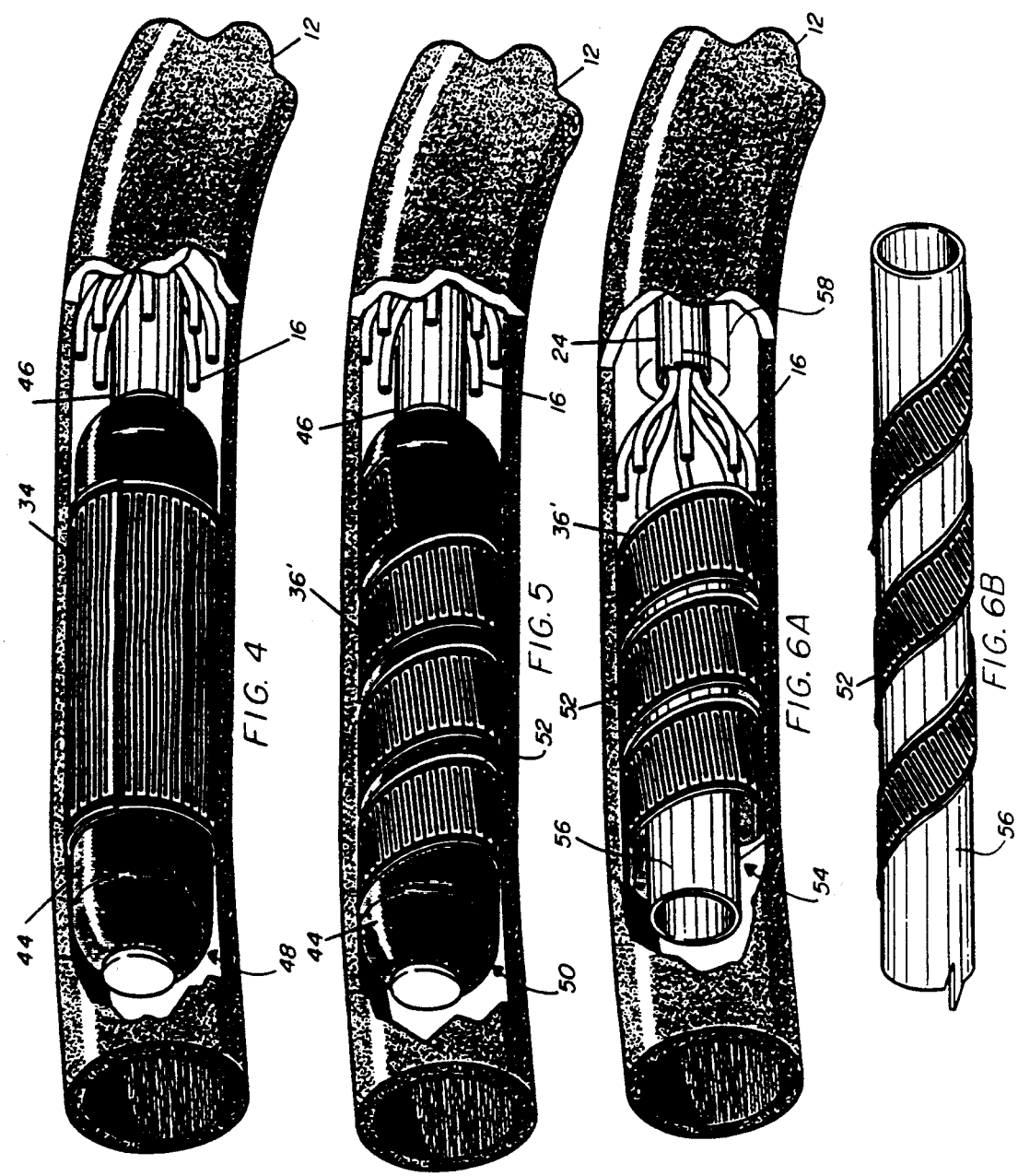

ELECTROPORATION METHOD AND APPARATUS FOR INSERTION OF DRUGS AND GENES INTO ENDOTHELIAL CELLS

BACKGROUND OF THE INVENTION

The present invention relates to the treatment of ailments in humans and other mammals, and more particularly, to a method and apparatus for delivering pharmaceutical compounds and genes into the endothelial cells of a patient.

Endothelial cells are in direct contact with the blood stream and cover almost one thousand square meters of the inner surface of the blood cells of a human. Damage to endothelial cells has been linked to cardiovascular diseases such as arteriosclerosis and high blood pressure. Endothelial cell damage may result from surgical procedures such as heart transplantation. More commonly damage to this type of cells is caused by balloon angioplasty and routing of the blood vessels with rotary and laser catheters. These procedures are frequently used to remove blockage in the coronary arteries, however, the resulting trauma and scarring to the lumen walls can lead to rapid return of fatty deposits and a recurrence of blockage. Genetic modification of the endothelial cells might correct the damage caused by surgical procedures and could reduce the rate of deposit of low density cholesterol before and after surgical procedures. Insertion of drugs directly into the endothelial cells might alleviate problems associated with damage to these cells.

SUMMARY OF THE INVENTION

Accordingly, it is an object of the present invention to provide a method of electroporation mediated, in vivo, drug and gene delivery into the endothelial cells of a patient.

It is another object of the present invention to provide an apparatus for electroporation mediated, in vivo, intra cellular drug and gene delivery into the endothelial cells of a patient.

According to the present invention a catheter device is inserted into a selected blood vessel of a patient and advanced to a preselected location within the blood vessel where the endothelial cells on the inner wall of the vessel are to be treated. Once in place, the catheter device is expanded so that a plurality of axially extending, circumferentially spaced electrodes carried thereby are in contact with the inner wall of the blood vessel. A fluid medium is then infused into the blood vessel adjacent the electrodes via a conventional pump. A power pack connected to the electrodes is energized to apply a predetermined electric signal to the electrodes. This subjects the endothelial cells to electric fields of predetermined amplitude and duration in order to make the walls of the endothelial cells transiently permeable to permit therapeutic genes or drugs carried by the fluid medium to enter the endothelial cells without killing them.

BRIEF DESCRIPTION OF THE DRAWINGS

Throughout the drawing figures like reference numerals refer to like parts.

FIG. 1 illustrates a first embodiment of the apparatus of the present invention implanted in a blood vessel.

FIG. 2 illustrates a second embodiment of the apparatus of the present invention implanted in a blood vessel.

FIG. 3 illustrates a third embodiment of the apparatus of the present invention implanted in a blood vessel.

FIG. 4 illustrates a fourth embodiment of the apparatus of the present invention implanted in a blood vessel.

FIG. 5 illustrates a fifth embodiment of the apparatus of the present invention implanted in a blood vessel.

FIG. 6A illustrates a sixth embodiment of the apparatus of the present invention implanted in a blood vessel.

FIG. 6B illustrates the sixth embodiment of the apparatus of the present invention in its retracted configuration in which it has a smaller insertion diameter.

DESCRIPTION OF THE PREFERRED EMBODIMENTS

Referring to FIG. 1, a first embodiment of our apparatus includes a catheter device 10 which is implanted in the blood vessel 12 of a patient which is to receive therapeutic treatment. The device includes a plurality of axially extending, circumferentially spaced pairs of electrodes 14 for repeatedly generating electric fields of a predetermined amplitude and duration. The catheter device 10 has a plurality of circumferentially spaced injection tubes 16 which deliver a fluid medium carrying preselected macromolecules such as genes or pharmacological compounds for introduction into the blood vessel 12 adjacent the electrodes 14. The electric fields are generated by applying a predetermined electric signal to the electrodes 14. The parameters of the signal are selected so that a quantity of blood flowing within the selected blood vessel is subjected to short pulses of high intensity electric fields. These fields make the endothelial cells on the inner wall of the blood vessel transiently permeable to permit the macromolecules to enter the endothelial cells without killing them. The permeability results from the temporary formation of pores in the cell walls which are large enough to permit trans-migration of the macromolecules.

Each of the electrodes 14 comprises a metal strip supported on an underlying non-conductive strip 18. The strips 18 may be made of a plastic material such as that sold under the trademark TEFLON so that the catheter device 10 can be surgically implanted within the surrounding blood vessel 12 with minimal complications from blood clotting. The electrodes 14 are also preferably coated with a semi-permeable layer to impede localized blood clotting. TEFLON material has pores which are too small to permit blood cells to pass through the same, but the pores are large enough for ions to carry the electroporation current.

The distal ends of the plastic strips 18 taper inwardly and are joined at their distal ends by a cap 20 which forms an insertion tip for the catheter device. The proximal ends of the plastic strips 18 also taper inwardly and are joined to a sleeve 22 which fits inside the outer protective sheath or casing 24 of a cable (not visible). The forward end of the cable is connected to the cap 20 and may be pulled rearwardly towards the catheter insertion point in order to expand the plastic strips 18 radially outwardly, thereby placing the electrodes 14 in contact with the endothelial cells on the inner wall of the blood vessel 14.

The electrodes 14 are connected via wires which extend within the casing 24. These wires are illustrated diagrammatically as phantom lines 26. The wires 26 are connected to a power pack 28 outside the patient's body. The power pack is illustrated diagrammatically in FIG. 1 as a box labeled PWR. It supplies the predetermined electrical signals to the electrodes 14 which are required to generate the desired electrical fields. A supply pump 30 mounted outside the patient's body supplies the fluid medium carrying the drugs or genes through the injection tubes 16 which are also enclosed by the casing 24. The supply pump is also illustrated diagrammatically as a box labeled P in FIG. 1. It may be of the conventional type that employs a syringe for holding a predetermined quantity of the fluid medium.

The catheter device 10 can be inserted into the selected blood vessel 12 and advanced to a preselected location within the blood vessel where the endothelial cells on the inner wall of the vessel are to be treated. Once in place, the catheter device is expanded so that the electrodes 14 are in contact with the inner wall of the blood vessel. The fluid medium is then infused into the blood vessel adjacent the electrodes 14 via pump 30. The power pack 28 is energized to apply a predetermined electric signal to the electrodes 14 thereby subjecting the endothelial cells to electric fields of predetermined amplitude and duration in order to make the walls of the endothelial cells transiently permeable to permit genes or drugs carried by the fluid medium to enter the endothelial cells without killing them.

Where genes are to be infused into the patient, the fluid medium is selected so that it will support the viability of the genes until they are inserted into the blood cells of the patient. Such fluid mediums are well known to those skilled in the art. The plunger of the syringe may be pushed inwardly by a motor driven piston assembly. The rate of delivery of the fluid medium from the syringe through the injection tubes may be manually adjusted via controls with the delivery parameters being indicated on a display.

The function of the power pack 28 is to generate a predetermined electric signals which, when applied to the electrodes 14, result in applying electric fields of a predetermined amplitude and duration so that the drugs or genes can enter the endothelial cell walls via electroporation. Preferably these fields are applied repeatedly and their amplitude and duration make the walls of the endothelial cells sufficiently permeable to permit the drugs or genes to enter the endothelial cells without killing them.

One suitable power pack is the ELECTRO CELL MANIPULATOR Model ECM 600R signal generator commercially available from BTX, Inc. of San Diego, Calif., U.S.A. The ECM 600 signal generator generates a pulse from the complete discharge of a capacitor which results in an exponentially decaying waveform. The electric signal generated by the ECM 600R signal generator is characterized by a fast rise time and an exponential tail. In the ECM 600R signal generator, the electroporation pulse length is set by selecting one of ten timing resistors marked R1 through R10. They are active in both High VM (capacitance fixed at fifty microfarads) and Low VM (with a capacitance range from 25 to 3,175 microfarads).

The passage of an electrical current across the cell membrane results in the creation of transient pores which are critical to the electroportion process. The ECM 600R signal generator provides the voltage (in kV) that travels across the gap (in cm) between the adjacent pairs of electrodes 14. This potential difference defines what is called the electric field strength where E equals kV/cm. Each cell species has its own critical field strength for optimum electroportion. This is due to cell size, membrane make-up and individual characteristics of the cell wall itself. For example, some Gram positive bacteria are quite resistant to electroporation and require very high field strengths, i.e., greater than 17 kV/cm, before cell death and/or electroporation occurs. Generally, the required field strength varies inversely to the size of the cell.

The ECM 600R signal generator has a knob that permits the adjustment of the amplitude of the set charging voltage applied to the internal capacitors from 50 to 500 volts in low VM and from 0.05 to 2.5 kV in the High VM. The amplitude of the electrical signal is shown on a display incorporated into the ECM 600R signal generator. This device further includes a plurality of push button switches for controlling pulse length, in the LOW VM mode, by a simultaneous combination of resistors parallel to the output and a bank of seven selectable additive capacitors.

The ECM 600R signal generator also includes a single automatic charge and pulse push button. This button may be depressed to initiate both charging of the internal capacitors to the set voltage and to deliver a pulse to the flow-through chamber in an automatic cycle that takes less than five seconds. The manual button may be sequentially pressed to repeatedly apply the predetermined electric field to the mixture of blood and fluid medium or a repetitive charge/pulse mode may be selected with an adjustable repetition rate. By selecting the electrical parameters of the pulses, the preferred insertion into endothelial cells is possible.

The waveforms of the electrical signal provided by the signal generator in the power pack can be an exponentially decaying pulse, a square pulse, a unipolar oscillating pulse train or a bipolar oscillating pulse train. The electric field strength can be 0.2 kV cm to 20 kV/cm. The pulse length can be ten microseconds to one hundred milliseconds. There can be one to one hundred pulses per liquid volume element as it passes through the blood vessel 20. Of course the waveform, electric field strength and pulse duration are dependent upon the exact construction of the catheter device 10 and the type of macromolecules that are to enter the endothelial cells via electroporation.

FIG. 2 illustrates a second embodiment 32 of the catheter device which comprises a plastic cylinder 34 having a continuous meander or serpentine electrode 36 deposited on the external surface thereof. The plastic cylinder is a rectangular piece of plastic sheet material rolled onto itself and may be expanded by an internal pantograph 38 which is actuated by pulling rearwardly on a cable 40 which extends within casing 24. The circumferentially spaced injection tubes 16 also extend within the casing 24 and terminate adjacent to and upstream from the electrode 36, as in the first embodiment. The two ends of the electrode are connected to corresponding wires (not illustrated) which extend through the casing 24 to the power pack 28.

FIG. 3 illustrates a third embodiment 42 of the catheter device. In this version, the strips 18 carrying the spaced pairs of electrodes 14 are secured to a balloon 44 which is inflated and deflated through a hose 46. The hose also encloses the wires that are connected to the electrodes.

FIG. 4 illustrates a fourth embodiment 48 of the catheter device. In this version the plastic cylinder 34 of the second embodiment having the serpentine electrode 36 surrounds and is expanded by the balloon 44 of the third embodiment.

FIG. 5 illustrates a fifth embodiment 50 of the catheter device. A serpentine electrode 36' is carried by a helical-shaped plastic strip 52 which is expanded by the balloon 44.

FIG. 6A illustrates a sixth embodiment 54 which utilizes the helical-shaped plastic strip 52 and serpentine electrode 36' of the fifth embodiment. The strip 52 is expanded and contracted by rotating a center guide rod 56 and sliding it axially. The forward or distal end of the strip 52 is connected to the forward or distal end of the rod. The rearward end of the strip 52 is secured to a stationary sleeve 58 that surrounds the casing 24. The rod 56 is rotated and slid axially by turning cable 40 which is not visible in FIG. 6A. The contracted configuration of the helical-shaped strip 52 is illustrated in FIG. 6B.

While we have described preferred embodiments of our catheter device and our method for drug and gene delivery to endothelial cells, it should be understood that modifications and adaptations thereof will occur to persons skilled in the art. Therefore, the protection afforded our invention should only be limited in accordance with the scope of the following claims.

We claim:

1. An in vivo method of introducing macromolecules into endothelial cells of a patient for therapeutic purposes, comprising the steps of:

selecting a catheter device having a distal inflatable balloon portion, a plurality of spaced pairs of electrodes mounted on the distal inflatable balloon portion and infusion passages extending along the catheter device and terminating to the exterior of said device proximal said distal inflatable balloon portion;

implanting said catheter device having said plurality of spaced pairs of electrodes into a selected blood vessel of the patient, inflating said distal inflatable balloon portion so that the electrodes contact an inner wall of said blood vessel at spaced positions therein for generating an electric field adjacent said inner wall of the selected blood vessel at a preselected location to be treated;

infusing preselected macromolecules via said infusion passages into the selected blood vessel at the selected location; and applying a predetermined electric signal to the electrodes to repeatedly subject a plurality of endothelial cells at the predetermined location in the selected blood vessel to electric fields of a predetermined amplitude and duration in order to make the walls of the endothelial cells transiently permeable to permit the macromolecules to enter the endothelial cells without killing said cells.

2. A method according to claim 1 wherein the macromolecules are selected from the group consisting of genes and pharmacological compounds.

3. A method according to claim 1 wherein said electrodes are a plurality of axially extending, circumferentially spaced pairs of electrodes.

4. A method according to claim 3 wherein the catheter is first inserted into the selected blood vessel and then expanded to place the electrodes into contact with the endothelial cells.

5. A method according to claim 1 wherein the electric signal has a wave form selected from the group consisting of an exponentially decaying pulse, a square pulse, a unipolar oscillating pulse train and a bipolar oscillating pulse train.

6. A method according to claim 5 wherein each pulse has a duration of between approximately ten microseconds and one hundred milliseconds.

7. A method according to claim 5 wherein there are between approximately one pulse and one hundred pulses for a given location as the unit passes through the selected blood vessel.

8. A method according to claim 1 wherein the electric field has a strength of between approximately 0.2 kV/cm and 20.0 kV/cm.

9. An apparatus for introducing macromolecules into endothelial cells at a selected location within a blood vessel of a patient, comprising:

implantable catheter means having a distal inflatable balloon portion, infusion passages extending along said catheter means and terminating to the exterior of said catheter means proximal said distal inflatable balloon portion, a plurality of substantially axially extending, circumferentially spaced pairs of electrodes mounted on said distal inflatable balloon portion, the electrodes of each pair being positionable upon inflation of said distal balloon portion so that the electrodes contact an inner wall of said blood vessel for generating an electric field at a predetermined location within a selected blood vessel of a patient;

means including said infusion passages for injecting a predetermined quantity of a fluid medium carrying preselected macromolecules into the selected blood vessel at the predetermined location; and means for applying an electric signal to the electrodes of the implantable catheter means for causing said electrodes to repeatedly generate electric fields of a predetermined amplitude and duration sufficient to make the walls of a plurality of endothelial cells at the predetermined location in the selected blood vessel to be transiently permeable to permit the macromolecules to enter said endothelial cells without killing said cells.

10. An apparatus according to claim 9 wherein the means for injecting the quantity of fluid carrying the macromolecules includes a pump.

11. An apparatus according to claim 9 wherein the means for applying electric fields to the blood includes a signal generator for generating the electric signal.

12. An apparatus according to claim 9 wherein the implantable means includes means for expanding the electrodes against the endothelial cells.

13. An apparatus according to claim 9 wherein implantable catheter means includes a split plastic cylinder carrying said electrodes on an external surface of the cylinder.

14. An apparatus, for introducing macromolecules into endothelial cells at a selected location within a blood vessel of a patient, comprising:

implantable means including a plurality of axially extending circumferentially spaced electrodes supported on a plurality of axially extending non-conductive strips which are circumferentially spaced and joined at their opposite ends, and means for expanding the electrodes including a cable connected to a distal set of ends of the strips for pulling the same toward a proximal set of ends of the strips, for expanding the electrodes against the endothelial cells for generating an electric field at a predetermined location within a selected blood vessel of a patient;

means for injecting a predetermined quantity of a fluid medium carrying preselected macromolecules into the selected blood vessel at the predetermined location; and means for applying an electric signal to the implantable means for causing it to repeatedly generate electric fields of a predetermined amplitude and duration in order to make the walls of a plurality of endothelial cells at the predetermined location in the selected blood vessel to be transiently permeable to permit the macromolecules to enter said endothelial cells without killing said cells.

15. An apparatus for introducing macromolecules into endothelial cells at a selected location within a blood vessel of a patient, comprising:

implantable means for generating an electric field at a predetermined location within a selected blood vessel of a patient, said implantable means including a split plastic cylinder carrying a serpentine electrode on an external surface of the cylinder and a pantograph positioned inside the cylinder for expanding the cylinder;

means for injecting a predetermined quantity of a fluid medium carrying preselected macromolecules into the selected blood blood vessel at the predetermined location; and means for applying an electric signal to the implantable means for causing it to repeatedly generate electric fields of a predetermined amplitude and duration in order to make the walls of a plurality of endothelial cells at the predetermined location in the selected blood vessel to be transiently permeable to permit the macromolecules to enter said endothelial cells without killing said cells.

16. An apparatus for introducing macromolecules into endothelial cells at a selected location within a blood vessel of a patient, comprising:

implantable means for generating an electric field at a predetermined location within a selected blood vessel of a patient wherein the implantable means includes a helical-shaped plastic strip with a serpentine electrode on an external surface thereof and means for expanding a diameter of the helical-shaped strip;

means for injecting a predetermined quantity of a fluid medium carrying preselected macromolecules into the selected blood blood vessel at the predetermined location; and means for applying an electric signal to the implantable means for causing it to repeatedly generate electric fields of a predetermined amplitude and duration in order to make the walls of a plurality of endothelial cells at the predetermined location in the selected blood vessel to be transiently permeable to permit the macromolecules to enter said endothelial cells without killing said cells.

17. An apparatus according to claim 16 wherein the expanding means includes a balloon.

18. An apparatus according to claim 16 wherein the expanding means includes a rotatable and axially moveable center guide rod positioned inside the helical-shaped strip.

* * * * *